United States Patent [19]

Rydell

[11] Patent Number: 5,352,222
[45] Date of Patent: Oct. 4, 1994

[54] SURGICAL SCISSORS WITH BIPOLAR COAGULATION FEATURE

[75] Inventor: Mark A. Rydell, Golden Valley, Minn.

[73] Assignee: Everest Medical Corporation, Minneapolis, Minn.

[21] Appl. No.: 213,671

[22] Filed: Mar. 15, 1994

[51] Int. Cl.⁵ .............................. A61B 17/39
[52] U.S. Cl. ........................ 606/37; 606/45; 606/52; 606/170; 606/174
[58] Field of Search ............ 606/27, 29, 32, 34, 606/37, 39, 40, 41, 45, 46, 47, 48, 49, 50, 51, 52, 167, 170, 171, 174, 175

[56] References Cited

U.S. PATENT DOCUMENTS

| | | | |
|---|---|---|---|
| 5,147,356 | 9/1992 | Bhatta | 606/37 |
| 5,312,434 | 5/1994 | Crainich | 606/45 X |

FOREIGN PATENT DOCUMENTS

| | | | |
|---|---|---|---|
| 517244 | 12/1992 | European Pat. Off. | 606/37 |
| 518230 | 12/1992 | European Pat. Off. | 606/37 |

*Primary Examiner*—Peter A. Aschenbrenner
*Attorney, Agent, or Firm*—Haugen and Nikolai

[57] ABSTRACT

A bipolar electrosurgical scissors for use in open or endoscopic surgery has a pair of opposed blade members pivotally joined to one another and to the distal end of the scissors itself by a rivet which extends through a insulated bushing member. Each of the blade members comprises a blade support and a blade itself, each fabricated from metal, such as stainless steel. The blades are affixed to their associated supports by means of a suitable adhesive or adhesive composite material such as a fiberglass reinforced epoxy exhibiting dielectric properties. Cutting is performed, steel-on-steel, without causing a short circuit between the two blade supports which themselves function as the bipolar electrodes.

11 Claims, 1 Drawing Sheet

SURGICAL SCISSORS WITH BIPOLAR COAGULATION FEATURE

BACKGROUND OF THE INVENTION

1. Field of the Invention

This invention relates generally to the design of a bipolar electrosurgical scissors, and more particularly to a surgical scissors incorporating bipolar electrodes as its blade elements, such that mechanical cutting with subsequent electrocoagulation can be achieved without requiring an instrument exchange.

2. Discussion of the Prior Art

Electrocoagulating instruments include at least one conductive electrode. Radio frequency energy is conducted through this electrode to either a remote conductive body-plate (monopolar) or to a second, closely-spaced conductive electrode (bipolar). Current passing through the gap between the two electrodes will coagulate blood and other body fluids placed between them.

Monopolar electrocautery instruments suffer from the fact that the return path between the active-electrode and the large area body-plate can be unpredictable as the electrical current seeks the return electrode through the path of least resistance. With bipolar electrosurgical instruments, however, because the two electrodes are closely spaced to one another, usually at the distal end of an instrument handle, the return path is very short and only involves the tissue and fluids in the short path between the electrodes.

There is available in the prior art a scissors-type instrument for mechanically snipping tissue during the course of an endoscopic procedure. Such a scissors comprises of pair of blades fabricated from metal and disposed at the distal end of an elongated tubular member whose outside diameter is sufficiently small to allow it to be passed through the working lumen of an endoscope, a laparoscope or other similar devices known in the art. Disposed at the proximal end of the rigid tube is a scissors-type handle having a pair of members, each with a finger-receiving loop therein which are pivotally coupled to one another. An appropriate linkage is made between the handle members and the blades so that manipulation of the handle members will result in an opening and closing of the blades relative to one another. When using a mechanical cutting scissors of this type to excise tissue, when a blood vessel is cut, bleeding results. At that point, it is generally necessary for the surgeon to remove the scissors instrument from the working lumen of the endoscope and then insert an electrocoagulator down the endoscope to the site of the bleeder. This instrument exchange is time-consuming and in a surgical procedure where moments count, it would be desirable to have a scissors-type instrument for cutting but which also incorporates the ability to coagulate blood and other body tissue using RF energy.

There is also available in the prior art monopolar scissors where both of the scissors blades form one pole and with a remote body plate being the second pole. To date, however, there is not available in the marketplace a bipolar electrosurgical scissors where its two blades are electrically isolated from one another and comprise the bipolar electrode pair. With metal-to-metal contact along the sharpened edges of the two blades, an electrical short results. Furthermore, the attempt to use a rivet or screw as the pivot point for the blades is another area where short-circuiting is likely to occur. When such a short exists, the electrical current does not flow through the blood or body tissue to effect coagulation, but instead, follows the short-circuit path from one electrode to the other.

In a copending application, Ser. No. 07/887,212, filed May 26, 1992, there is described a bipolar scissors for insertion into a laparoscope, trocar or endoscope for effecting electrocoagulation of blood and tissue during laparoscopic or other endoscopic surgery. The scissors blades at the distal tip of the instrument perform cutting of the tissue by mechanical shearing action. The two blades are effectively insulated from one another, allowing them to function as bipolar electrodes for electrocoagulating small blood vessels in the surgical field.

The instrument of the aforereferenced application includes a scissors-type handle having first and second pivoting members, each with a finger-receiving loop on one end of each and extending from the opposite end of one is an elongated, rigid tubular member of a size capable of being inserted through the trocar or endoscope. Affixed to the distal end of the rigid tubular member is a first blade composite which comprises a metal blank having a suitable ceramic layer bonded to one major surface thereof, the ceramic being honed to define a sharp cutting edge. Pivotally joined to the first blade by an insulating pivot member is a second blade composite, also having a metal blank with a ceramic substrate bonded to one major surface thereof. When the two blade blanks are pivotally joined together, the ceramic layers are in face-to-face relationship and because the cutting edges thereof are honed, the blades are capable of cutting tissue when made to move in a scissors-like manner with tissue placed between the cutting edges thereof.

Extending through the lumen of the elongated tubular member is a wire or rod which is rigid in the longitudinal direction and which is coupled at its proximal end to one of the handle members and at its other end to one of the scissors blades. By appropriately manipulating the handle members, a snipping action of the blades results.

The instrument further includes means for applying a RF voltage across the gap between the two metal blade blanks which are maintained separated from one another by the ceramic faces bonded to these blanks. As such, the blades of the instrument itself can be used as a bipolar electrocoagulation device, obviating the need for doing an instrument exchange when it is necessary to coagulate blood and tissue following the mechanical cutting thereof.

In copending application Ser. No. 08/092,076, filed Jul. 16, 1993, there is described a bipolar electrosurgical scissors having curved blades in the embodiments of each of the aforereferenced applications, the bipolar blades are constructed by appropriately adhering a specially ground ceramic insulating member defining the sheering surface and cutting edge of the scissors to metal electrodes where it is the ceramic surfaces that interact with one another to perform the cutting function as the blades are opened and closed relative to one another. While that arrangement works well in implementing a bipolar electrosurgical scissors, the cost of manufacture is relatively high because of the difficulty in working with ceramics, especially when constructing electrosurgical scissors having arcuate blades. Those skilled in the art appreciate that ceramic will readily fracture when subjected to bending forces and, hence, it is necessary to produce the requisite ceramic elements for the scissors in a series of grinding operations.

A need therefore exists for a bipolar electrosurgical scissors for use in both open and endoscopic surgical procedures where the shearing surfaces may be surgical steel, but where the blades can also be used in performing bipolar electrocoagulation as the cutting progresses.

SUMMARY OF THE INVENTION

It is accordingly a principal object of the present invention to provide a bipolar, electrocoagulating instrument having metal scissors blades for the mechanical cutting of tissue.

Another object of the present invention is to provide a pair of bipolar scissors having a miniaturized distal blade configuration that allows the instrument to be inserted through a laparoscope, trocar or the working lumen of an endoscope.

Still another object of the present invention is to provide a bipolar-type scissors instrument having metal (stainless steel) cutting surfaces and which utilizes a push rod and pivot combination to cause movement of the scissors blade through manipulation of a scissors-style handle mechanism at the proximal end of the instrument and wherein blade supports for the scissors may be simultaneously energized from a RF source to effect the electrocoagulation of cut tissue.

The foregoing object of the invention is achieved by providing an instrument having a metal blade member with a sheering surface and a honed cutting edge. The blade member is affixed to a metal blade support by an electrically insulating bonding layer which is disposed intermediate the blade member and the blade support. In forming an endoscopic scissors, this blade assembly is pivotally secured to the distal end of an elongated tube. An actuating link extends through the tube to a movable portion of a scissors handle so that when the handle is manipulated, the blades can be made to open and close relative to one another in scissors-like fashion. Also extending through the lumen from electrical terminals on the handle to the metal blade supports are conductors which permit a voltage to be applied between the two blade supports. Because the blade having the sharpened edge and shearing surface is insulated from its blade support, there will be no short circuit between the blade members due to the fact that the conductive shearing surfaces come into contact with one another along their length as the blades are closed on an object to be cut.

It has been found convenient in the manufacture of the scissors of the present invention to employ a partially cured epoxy, an epoxy impregnated fiberglass mat or a slurry of glass beads and epoxy as the bonding layer for joining the blades to their respective supports while maintaining a desired spacing therebetween. The partially cured epoxy can be die-cut to size so as to conform in shape to the interface between the blade support and the blade member. When the laminated structure is clamped together and then subjected to a heating operation, the epoxy spacer layer fully cures and creates a strong bond between the blade and its blade support, while still maintaining electrical isolation therebetween.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
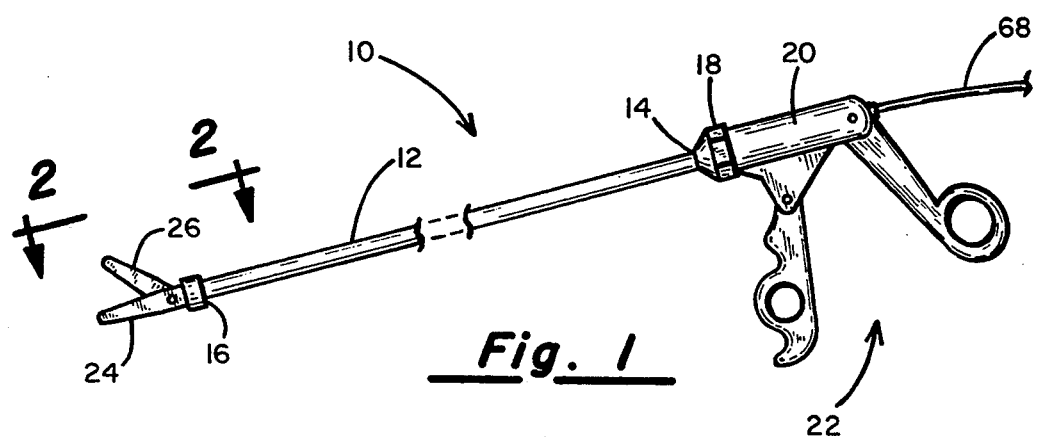
FIG. 1 is a perspective view of an endoscopic electrosurgical scissors constructed in accordance with the present invention.

Referring to FIG. 1, there is indicated generally by numeral 10 a bipolar electrosurgical scissors for endoscopic surgery constructed in accordance with the present invention. It is seen to include an elongated tubular barrel 12 having a proximal end 14, a distal end 16 and with a lumen extending therebetween. The O.D. of the barrel is sufficiently small to be passed through the working lumen of an endoscope (laparoscope). Affixed to the proximal end 14 of the bipolar scissors 10 is a rotatable knob 18 appropriately mounted in the stationary portion 20 of a scissors handle assembly 22 so that the knob 18 can be rotated, the barrel 12 turning with it. Those desiring further details on the construction and internal workings of the handle assembly 22 are referred to applicant's earlier patent application Ser. No. 08/013,852, filed Feb. 5, 1993. That application describes in detail how manipulation of the scissors handle 22 causes blades 24 and 26 connected to the distal end 16 of the tube 12 to move in scissors-like action relative to one another. Because the novel features of the present invention center on the construction of the blades 24 and 26, there is no need to further describe the details of the handle construction.

Figure 2:
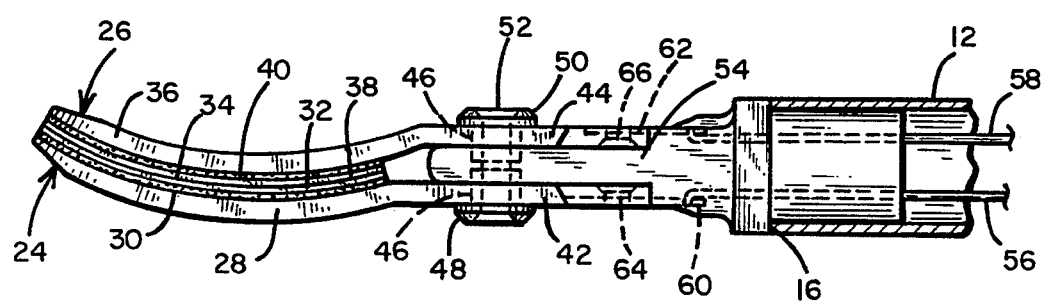
FIG. 2 is a greatly enlarged top view of the distal end portion of the scissors of FIG. 1.

Referring to FIG. 2, there is shown a greatly enlarged top plan view of the distal end portion of the scissors viewed along the line 2—2 in FIG. 1. Blade 24 is seen to comprise a conductive metal blade support 28, preferably fabricated from stainless steel. While the blade support 28 is illustrated as having an arcuate profile when observed from the top as in FIG. 2, it can just as well be straight. Attached to the blade support by means of a dielectric bonding agent 30 is a metal blade 32 having an arcuate shearing surface 34 and a honed cutting edge.

In adhering the cutting blade 34 to the blade support 28, it has been found convenient to employ a suitable epoxy, such as AF 125 sold by the 3M Company because of its desired dielectric characteristics. The epoxy bonding/spacing layer 30 may be obtained in a partially cured state so that it is rigid enough to hold its own shape, but can easily be die-cut to a desired size and shape characteristic. The partially cured epoxy layer is then applied against the concave surface of the blade support 28 and because in the partially cured state, the material is tacky, it will adhere to it. Next, the blade 34, itself, is pressed against the other side of the partially cured epoxy bonding layer 30 and when appropriately aligned, a suitable clamp is used to hold the assembly together. The assembly may then be placed in an oven or otherwise heated to the point where the epoxy layer becomes fully cured and hard. When the assembly is removed from the oven and the clamp is removed, it is found that a very strong bond holds the blade 34 to the support 28. The two are electrically insulated from one another, however, by the epoxy bonding layer.

To ensure that clamping and heating does not alter the width of the insulating gap, a fiberglass mat of the desired thickness can be impregnated with a B-stage type epoxy or glass beads of a diameter corresponding to the desired gap width can be mixed with the B-stage epoxy before it is interposed between the blade and its support and prior to the clamping and heat curing thereof.

The other scissors blade 26 is manufactured in much the same fashion. It includes a blade support 36 and a blade member 38 bonded together by a dielectric bonding/spacing layer 40. The dielectric bonding/spacing layer is again preferably an epoxy or a glass-filled epoxy material adhered to the convex surface of the blade support 36.

The proximal end portions 42 and 44 of the blade supports 28 and 36 each have a circular aperture extending therethrough as at 46 and fitted into each of the apertures is an insulating bushing half 48–50 allowing a steel rivet 52 to pivotally secure the blades 24 and 26 to an insulating hub 54 without creating an electrical short circuit between the blade supports 28 and 36. The hub member 54 fits within the distal end 16 of the tubular barrel 12 and is appropriately bonded or swagged so as not to come loose.

The mechanism for actuating the blades 24 and 26 in a scissors-like motion is similar to that described in applicant's earlier copending application Ser. No. 08/013,852, which is herein incorporated by reference. In that arrangement, first and second conductive rods 56 and 58 extend through the lumen of the barrel 12 from the scissors handle members to a pair of conductive links 60 and 62. The links are pivotally secured to the distal ends of the rods 58 and 60 and to the blade halves 24 and 26 by means of conductive metal rivets 64 and 66. The rivets 64 and 66 pass through apertures formed in the distal end portions of the blade halves 24 and 26 at locations that are off of center so that a lever arm is created for moving the blades as the conductive rods 56 and 58 are reciprocally, longitudinally displaced by actuation of the scissors handle 22. A slip-ring connection is provided in the handle portion 20 for allowing conductors in the insulated electrical cord 68 (FIG. 1) to join to the conductive rods 56 and 58 while still permitting the barrel 12 to be rotated upon turning the knob 18 and without twisting the conductors in lead 68. In this fashion, a predetermined RF voltage may be applied across the blade supports 28 and 36 by way of the lead 68, the conductive rods 56 and 58, the links 60 and 62 and the rivets 64 and 66. Because of the insulating layers 30 and 40 used in bonding the sharpened blades 32 and 38 to the blade supports 28 and 36, those two blades can touch one another along their entire length as the cutting motion takes place without creating an electrical short circuit therebetween. When it is desired to cauterize tissue, the RF voltage is applied to the electrosurgical scissors, thereby making the blade supports the active bipolar electrodes. When the two blade supports are brought into contact with tissue, a current flows from the first blade support, through the tissue to the second blade support, thereby effecting cauterization.

The present invention obviates the need for providing a somewhat fragile ceramic layer to define the shearing surface and cutting edges of the blades. The stainless steel blade supports and the blades themselves can be readily bent to create a curved blade without the need for expensive grinding operations heretofore necessary in creating curved ceramic pieces.

The use of a partially cured epoxy dielectric adhesive in the early stages of fabrication for adhering the blade to its support and then later fully curing the epoxy layer also greatly simplifies the steps needed to manufacture an electrosurgical scissors having bipolar electrodes.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself. For example, while an endoscopic scissors has been used in explaining the invention, it is equally applicable to a scissors designed for open surgery. Hence, the scope of the invention is to be determined from the appended claims.

What is claimed is:

1. A bipolar electrosurgical instrument for cutting and coagulating tissue comprising:
   (a) first and second blade members each comprising a laminated assembly of a metal blade defining a shearing surface, a metal blade support and an intermediate electrically insulative bonding/spacing layer for joining said blade to said blade support;
   (b) means for pivotally joining said first and second blade members together with their respective shearing surfaces facing one another;
   (c) means coupled to at least one of said first and second blade members for imparting a scissors-like movement relative to the other of said first and second blade members; and
   (d) means for applying a voltage between the metal blade supports of said first and second blade members.

2. The bipolar electrosurgical instrument as in claim 1 wherein said shearing surfaces of said first and second blade members and said blade support are curved.

3. The bipolar electrosurgical instrument as in claim 2 wherein said intermediate, electrically insulating bonding/spacing layer is an epoxy material.

4. The bipolar electrosurgical instrument as in claim 3 wherein said epoxy material includes a fiberglass-mat of a predetermined thickness therein.

5. The bipolar electrosurgical instrument as in claim 3 wherein said epoxy material includes glass microspheres of a predetermined maximum diameter therein.

6. The bipolar electrosurgical instrument as in claim 3 wherein said metal is stainless steel.

7. A bipolar electrosurgical instrument for cutting and coagulating tissue comprising, in combination:
   (a) an elongated tubular member having a proximal end, a distal end and a lumen extending therebetween;
   (b) first and second blade members, each comprising a laminated assembly of a metal blade defining a shearing surface, a metal blade support and an intermediate electrically insulating spacing/bonding layer for joining said blade to said blade support;
   (c) means for pivotally joining said first and second blade members to the distal end of said elongated tubular member with their respective shearing surfaces facing one another;

(d) a handle affixed to said proximal end of said tubular member;

(e) means coupled to said handle and extending through said lumen for imparting a scissors-like movement to at least one of said first and second blade members relative to the other; and (f) means extending through said lumen for applying a voltage between said blade supports of said first and second blade members.

8. The bipolar electrosurgical instrument as in claim 7 wherein said intermediate electronically insulating bonding layer is an epoxy material.

9. The bipolar electrosurgical instrument as in claim 8 wherein said epoxy material includes a fiberglass-mat of a predetermined thickness therein.

10. The bipolar electrosurgical instrument as in claim 8 wherein said epoxy material includes glass microspheres of a predetermined maximum diameter therein.

11. The bipolar electrosurgical instrument as in claim 7 wherein said first and second blade members are curved.

* * * * *